United States Patent
Fleming et al.

(10) Patent No.: US 10,092,905 B2
(45) Date of Patent: Oct. 9, 2018

(54) TISSUE SAMPLE CONTAINER AND METHODS

(71) Applicant: LEICA BIOSYSTEMS NUSSLOCH GMBH, Nussloch (DE)

(72) Inventors: Jo Fleming, Boulder, CO (US); Charles E. Clemens, Encinitas, CA (US); David Berardelli, San Diego, CA (US)

(73) Assignee: Leica Biosystems Nussloch GmbH, Nussloch (DE)

( * ) Notice: Subject to any disclaimer, the term of this patent is extended or adjusted under 35 U.S.C. 154(b) by 330 days.

(21) Appl. No.: 14/406,899

(22) PCT Filed: Jun. 24, 2013

(86) PCT No.: PCT/US2013/047293
§ 371 (c)(1),
(2) Date: Dec. 10, 2014

(87) PCT Pub. No.: WO2013/192607
PCT Pub. Date: Dec. 27, 2013

(65) Prior Publication Data
US 2015/0158027 A1   Jun. 11, 2015

Related U.S. Application Data

(60) Provisional application No. 61/663,326, filed on Jun. 22, 2012, provisional application No. 61/792,929, filed on Mar. 15, 2013.

(51) Int. Cl.
*A61B 10/00* (2006.01)
*B01L 3/00* (2006.01)
*G01N 1/36* (2006.01)

(52) U.S. Cl.
CPC ...... *B01L 3/50853* (2013.01); *A61B 10/0096* (2013.01); *B01L 3/502715* (2013.01);
(Continued)

(58) Field of Classification Search
CPC ........................................ C12M 3/00
(Continued)

(56) References Cited

U.S. PATENT DOCUMENTS 3,319,289 A * 5/1967 McCormick ........... B23Q 3/086
264/138
3,792,699 A   2/1974 Tobin et al.
(Continued)

FOREIGN PATENT DOCUMENTS

CN   1898022 A   1/2007
CN   101300471 A   11/2008
(Continued)

OTHER PUBLICATIONS

Communication dated Feb. 19, 2016, from the European Patent Office in counterpart European application No. 13806432.4.
(Continued)

*Primary Examiner* — Dean Kwak
(74) *Attorney, Agent, or Firm* — Sughrue Mion, PLLC

(57) ABSTRACT

A tissue sample container including a base having a plurality of sample holding sections, which are configured to receive a plurality of tissue samples in a given orientation and are demarcated by section walls; and a lid configured to sealingly engage the base. The sample holding sections are sized and shaped to correspond to a specific tissue sample size and shape such that the base in cooperation with the section walls, maintain the given orientation and identity of the tissue samples within respective sample holding sections.

24 Claims, 11 Drawing Sheets

(52) U.S. Cl.
CPC .............. *B01L 3/545* (2013.01); *G01N 1/36* (2013.01); *B01L 2300/04* (2013.01); *F04C 2270/041* (2013.01); *G01N 2001/368* (2013.01)

(58) Field of Classification Search
USPC ............................... 422/536, 547; 83/915.5
See application file for complete search history.

(56) References Cited

U.S. PATENT DOCUMENTS

| | | | |
|---|---|---|---|
| 4,735,794 A | 4/1988 | Parkinson | |
| 5,401,625 A | 3/1995 | Robinson | |
| 5,427,742 A * | 6/1995 | Holland | G01N 1/36 |
| | | | 422/536 |
| 5,447,841 A | 9/1995 | Gray et al. | |
| 5,601,650 A | 2/1997 | Goldbecker et al. | |
| 5,667,985 A | 9/1997 | O'Leary et al. | |
| 5,695,942 A | 10/1997 | Farmilo et al. | |
| 5,817,032 A * | 10/1998 | Williamson, IV | |
| | | | A61B 10/0096 |
| | | | 422/536 |
| 5,895,628 A | 4/1999 | Heid et al. | |
| 5,965,454 A | 10/1999 | Farmilo et al. | |
| 5,968,436 A | 10/1999 | Takezaki | |
| 6,042,874 A | 3/2000 | Visinoni et al. | |
| 6,103,518 A | 8/2000 | Leighton | |
| 6,207,408 B1 | 3/2001 | Essenfeld et al. | |
| 6,270,464 B1 | 8/2001 | Fulton, III et al. | |
| 6,311,945 B1 | 11/2001 | DAngelo | |
| 6,329,645 B2 | 12/2001 | Giberson et al. | |
| 6,356,782 B1 | 3/2002 | Sirimanne et al. | |
| 6,372,512 B1 | 4/2002 | Kerschmann | |
| 6,383,801 B1 | 5/2002 | Leighton | |
| 6,444,170 B1 | 9/2002 | Heid et al. | |
| 6,465,245 B1 | 10/2002 | Walton et al. | |
| 6,468,783 B1 | 10/2002 | Leighton | |
| 6,513,803 B2 | 2/2003 | Morales et al. | |
| 6,521,186 B1 | 2/2003 | Izvortchikov et al. | |
| 6,586,713 B2 | 7/2003 | Essenfeld et al. | |
| 6,596,479 B1 | 7/2003 | Gray et al. | |
| 6,699,205 B2 | 3/2004 | Fulton, III et al. | |
| 6,793,890 B2 | 9/2004 | Morales et al. | |
| 6,797,928 B2 | 9/2004 | Giberson et al. | |
| 6,803,018 B1 | 10/2004 | Stiller | |
| 6,875,583 B2 | 4/2005 | Giberson et al. | |
| 6,902,928 B2 | 7/2005 | Izvortchikov et al. | |
| 6,991,934 B2 | 1/2006 | Walton et al. | |
| 7,005,110 B2 | 2/2006 | Taft et al. | |
| 7,075,045 B2 | 7/2006 | Visinoni | |
| 7,155,050 B1 | 12/2006 | Sloge et al. | |
| 7,156,814 B1 | 1/2007 | Williamson, IV et al. | |
| 7,179,424 B2 | 2/2007 | Williamson, IV et al. | |
| 7,217,392 B2 | 5/2007 | Bogen et al. | |
| 7,219,884 B2 | 5/2007 | Morales | |
| 7,229,417 B2 | 6/2007 | Foerster et al. | |
| 7,273,587 B1 | 9/2007 | Birkner et al. | |
| 7,273,720 B1 | 9/2007 | Birkner et al. | |
| 7,329,533 B2 | 2/2008 | Fredenburgh | |
| 7,470,401 B2 | 12/2008 | Morales | |
| 7,521,021 B2 | 4/2009 | McCormick | |
| 7,526,987 B2 | 5/2009 | Morales | |
| 7,544,953 B2 | 6/2009 | Goodman | |
| 7,547,538 B2 | 6/2009 | Morales et al. | |
| 7,553,672 B2 | 6/2009 | Bogen et al. | |
| 7,572,236 B2 | 8/2009 | Quick et al. | |
| 7,575,556 B2 | 8/2009 | Speeg et al. | |
| 7,576,307 B2 | 8/2009 | Yazdanfar et al. | |
| 7,584,019 B2 | 9/2009 | Feingold et al. | |
| 7,593,787 B2 | 9/2009 | Feingold et al. | |
| 7,603,201 B2 | 10/2009 | Feingold et al. | |
| 7,618,828 B2 | 11/2009 | Bleuel et al. | |
| 7,625,397 B2 | 12/2009 | Foerster et al. | |
| 7,657,070 B2 | 2/2010 | Lefebvre | |
| 7,663,101 B2 | 2/2010 | Goodman | |
| 7,666,620 B2 | 2/2010 | Wiederhold | |
| 7,687,255 B2 | 3/2010 | Chu | |
| 7,722,810 B2 | 5/2010 | Allen et al. | |
| 7,767,434 B2 | 8/2010 | Chu | |
| 7,776,274 B2 | 8/2010 | Williamson, IV et al. | |
| 7,780,919 B2 | 12/2010 | McCormick | |
| 7,850,912 B2 | 12/2010 | Favuzzi et al. | |
| 7,854,707 B2 | 12/2010 | Hibner et al. | |
| 7,881,517 B2 | 2/2011 | Sloge et al. | |
| 7,888,132 B2 | 2/2011 | McCormick | |
| 7,901,634 B2 | 3/2011 | Testa | |
| 7,914,462 B2 | 3/2011 | Hutchins et al. | |
| 7,914,738 B2 | 3/2011 | Hutchins et al. | |
| 8,118,775 B2 | 2/2012 | Grunewald et al. | |
| 2003/0170881 A1 | 9/2003 | Davis et al. | |
| 2005/0084425 A1 | 4/2005 | Williamson, IV et al. | |
| 2005/0112032 A1 | 5/2005 | McCormick | |
| 2005/0142631 A1 | 6/2005 | Mosconi et al. | |
| 2005/0147538 A1 | 7/2005 | Williamson, IV et al. | |
| 2006/0147896 A1 | 7/2006 | Schnetz et al. | |
| 2006/0177812 A1 | 8/2006 | Schnetz et al. | |
| 2006/0228772 A1 | 10/2006 | Donndelinger | |
| 2007/0072167 A1 | 3/2007 | Rochaix | |
| 2007/0104618 A1 | 5/2007 | Williamson, IV et al. | |
| 2007/0116612 A1 | 5/2007 | Williamson, IV | |
| 2007/0141711 A1 | 6/2007 | Stephens et al. | |
| 2007/0161609 A1 | 7/2007 | Buck et al. | |
| 2007/0166834 A1 | 7/2007 | Williamson, IV et al. | |
| 2007/0218542 A1 | 9/2007 | Li et al. | |
| 2008/0026366 A1 | 1/2008 | Harkins | |
| 2008/0138854 A1 | 6/2008 | Williamson | |
| 2008/0193014 A1 | 8/2008 | Ecker et al. | |
| 2008/0206807 A1 | 8/2008 | Duymelinck et al. | |
| 2008/0219885 A1 | 9/2008 | Horstman | |
| 2008/0220468 A1 | 9/2008 | Windeyer et al. | |
| 2008/0227144 A1 | 9/2008 | Nightingale | |
| 2008/0254504 A1 | 10/2008 | Vom et al. | |
| 2008/0268496 A1 | 10/2008 | Mosconi et al. | |
| 2008/0274496 A1 | 11/2008 | Duymelinck et al. | |
| 2009/0065368 A1 | 3/2009 | Davis et al. | |
| 2009/0098522 A1 | 4/2009 | Marcovitz | |
| 2009/0104692 A1 | 4/2009 | Bartfeld et al. | |
| 2009/0145920 A1 | 6/2009 | Kerrod et al. | |
| 2009/0165940 A1 | 7/2009 | Baur et al. | |
| 2009/0170152 A1 | 7/2009 | Reeser et al. | |
| 2009/0191544 A1 | 7/2009 | DeLa Torre Bueno | |
| 2009/0203066 A1 | 8/2009 | Perrut et al. | |
| 2009/0208105 A1 | 8/2009 | Bystrov et al. | |
| 2009/0222746 A1 | 9/2009 | Chirica et al. | |
| 2009/0253199 A1 | 10/2009 | McCormick | |
| 2010/0017030 A1 | 1/2010 | Feingold et al. | |
| 2010/0005563 A1 | 3/2010 | Konrad et al. | |
| 2010/0061632 A1 | 3/2010 | Young et al. | |
| 2010/0075410 A1 | 3/2010 | Desai et al. | |
| 2010/0092064 A1 | 4/2010 | Li | |
| 2010/0093023 A1 | 4/2010 | Gustafsson et al. | |
| 2010/0099140 A1 | 4/2010 | Donndelinger | |
| 2010/0106053 A1 | 4/2010 | Videbaek et al. | |
| 2010/0112624 A1 | 5/2010 | Metzner et al. | |
| 2010/0112625 A1 | 5/2010 | Erben et al. | |
| 2010/0144002 A1 | 6/2010 | Donndelinger | |
| 2010/0167334 A1 | 7/2010 | Williamson, IV | |
| 2010/0167338 A1 | 7/2010 | Amano et al. | |
| 2010/0182877 A1 | 7/2010 | Chu | |
| 2010/0184127 A1 | 7/2010 | Williamson, IV et al. | |
| 2010/0208955 A1 | 8/2010 | Mehes et al. | |
| 2010/0223935 A1 | 9/2010 | Donndelinger | |
| 2010/0248301 A1 | 9/2010 | Ulbrich et al. | |
| 2010/0278627 A1 | 11/2010 | Williamson, IV et al. | |
| 2010/0279341 A1 | 11/2010 | Steiner et al. | |
| 2010/0323395 A1 | 12/2010 | Ulbrich et al. | |
| 2010/0330660 A1 | 12/2010 | Hutchins et al. | |
| 2011/0008884 A1 | 1/2011 | Morales | |
| 2011/0034341 A1 | 2/2011 | Mehes et al. | |
| 2011/0045565 A1 | 2/2011 | Sanders et al. | |
| 2011/0054679 A1 | 3/2011 | Lefebvre et al. | |
| 2011/0060766 A1 | 3/2011 | Ehlke et al. | |

(56) References Cited

U.S. PATENT DOCUMENTS

| | | | |
|---|---|---|---|
| 2011/0076753 | A1 | 3/2011 | Goerner et al. |
| 2012/0065542 | A1 | 3/2012 | Hibner et al. |

FOREIGN PATENT DOCUMENTS

| | | | |
|---|---|---|---|
| CN | 101896274 A | | 11/2010 |
| CN | 102292030 A | | 12/2011 |
| DE | 102007011329 A1 | | 9/2008 |
| DE | 102008005265 A1 | | 7/2009 |
| DE | 102009010667 A1 | | 9/2010 |
| EP | 0807807 A1 | | 11/1997 |
| EP | 1508026 | | 2/2005 |
| EP | 1545775 | | 6/2005 |
| EP | 1682272 | | 7/2006 |
| EP | 1782737 A1 | | 5/2007 |
| EP | 1975595 A1 | | 10/2008 |
| EP | 1985383 A1 | | 10/2008 |
| EP | 2002894 A1 | | 12/2008 |
| EP | 2091440 | | 8/2009 |
| EP | 2 864 467 A1 | | 4/2015 |
| JP | 2007161307 A | | 6/2007 |
| JP | 2008-128749 A | | 6/2008 |
| JP | 2009150902 A | | 7/2009 |
| JP | 2011502254 A | | 1/2011 |
| WO | 0019897 A1 | | 4/2000 |
| WO | 2004/028693 A1 | | 4/2004 |
| WO | 2005/037182 A2 | | 4/2005 |
| WO | 2008/040812 A1 | | 4/2008 |
| WO | 2008/073387 A1 | | 6/2008 |
| WO | 2009/055605 A1 | | 4/2009 |
| WO | 2009055603 A2 | | 4/2009 |
| WO | 2010/030358 A1 | | 3/2010 |
| WO | 2010/085626 A1 | | 7/2010 |
| WO | 2010/112316 A1 | | 10/2010 |
| WO | 2011041495 A1 | | 4/2011 |
| WO | 2011/133453 A2 | | 10/2011 |
| WO | 2013192606 A1 | | 12/2013 |

OTHER PUBLICATIONS

English translation of communication dated Jun. 2, 2016, from the State Intellectual Property Office of the P.R.C., in counterpart Chinese application No. 201380032768.0.

International Search Report for PCT/US2013/047293 dated Oct. 17, 2013 [PCT/ISA/210].

Communication dated Oct. 14, 2015 from the State Intellectual Property Office of the People's Republic of China in counterpart application No. 201380032750.0.

English Translation of the Communication dated Jan. 24, 2017, from the Japanese Patent Office in counterpart Japanese application No. 2015-518635.

* cited by examiner

TISSUE SAMPLE CONTAINER AND METHODS

REFERENCE TO RELATED APPLICATION

Reference is hereby made to U.S. Provisional Patent Application Ser. No. 61/663,326, filed Jun. 22, 2012 and entitled BIOPSY TISSUE SAMPLE TRANSPORT DEVICE and U.S. Provisional Patent Application Ser. No. 61/792,929, filed Mar. 15, 2013 the disclosures of which is hereby incorporated by reference and priority of which is hereby claimed pursuant to 37 CFR 1.78(a)(4) and (5)(i).

FIELD OF THE INVENTION

The present disclosure relates generally to a tissue sample container, and in particular, to a tissue sample container configured to maintain the given orientation and identity of a tissue sample within the container.

BACKGROUND OF THE INVENTION

Biopsy is the removal of tissue to examine it for signs of cancer or other disorders. Biopsies may be open (surgically removing tissue) or percutaneous (e.g. by fine needle aspiration, core needle biopsy or vacuum assisted biopsy). The biopsy site can be located via palpation, ultrasound or mammography.

Biopsy samples are obtained in a variety of ways using various medical procedures involving a variety of the sample collection devices. Examples of collection devices include those marketed under the tradenames MAMMOTOME (from DEVICOR MEDICAL PRODUCTS, Cincinnati Ohio), CELERO, ATEC AND EVIVA (all from HOLOGIC, Malborough Mass.), and FINESSE and ENCOR (all from BARD BIOPSY SYSTEMS, Tempe Ariz.).

Some of these systems collect the tissue sample in a closed container. U.S. Pat. No. 8,118,775 describes a closed tissue sample storage container that is designed to spatially segregate biopsy samples during the collection procedure. U.S. Pat. No. 7,572,236 describes a biopsy device with a closed container for collecting one or more samples. The container includes a basket for flushing away blood and other tissue debris from the specimens.

After the samples are removed from the patient, a tissue marker can be inserted into the tissue site to later relocate the site, if needed. For example, U.S. Pat. Nos. 6,270,464, 6,356,782, 6,699,205, 7,229,417 and 7,625,397 all describes tissue markers and methods for marking a biopsy site. It is desirable to be able to later relocate the position that the sample was taken from the tissue site by correlating information retained with the sample against the tissue marker.

After a tissue sample is collected, the sample is analyzed at a lab (e.g. a pathology lab, biomedical lab, etc.) that is set up to perform the appropriate tests (such as histological analysis) Often, collection of the sample, and analysis of the sample are performed at different locations and the sample must be transported from the collection location (e.g. hospital, clinic, etc.) to the lab (e.g. a pathology lab, biomedical lab, etc) for analysis.

Thus, after collection, the tissue samples are typically removed from the collection container and placed into another container for transport to a lab. Currently, the sample may simply be placed loosely in a specimen jar filled with the fixing agent or chemical (e.g., a solution of formaldehyde in water such as Formalin), which preserves the tissue sample for analysis and the specimen jar sealed for shipping. If multiple samples are collected, multiple samples from the same patient may be placed in the same jar for transportation. It is desirable to retain information collected during the tissue with each sample.

Once the tissue sample arrives in the lab, a series of steps may be performed for processing the tissue sample including:

1—Fixation of the sample to immobilize molecular components and/or prevent degradation. This is typically done with a fixing agent or chemical (e.g., a solution of formaldehyde in water such as formalin) shortly after sample collection.

2—Transferring the sample from the transportation jar to a processing cassette.

3—Infiltrating the sample with an embedding material, such as the paraffin wax.

4—Embedding the sample in the paraffin wax.

5. Sectioning using for example a microtome by slicing the sample into a plurality of thin sections (e.g., 2 to 25μ thick sections), prior to performing any staining analysis.

Fixation is a process by means of which cell proteins are stabilized, and the process is normally performed using chemical fixatives. A good fixative is usually a fluid that will neither shrink nor swell the tissue, and more particularly will not dissolve its constituent parts, but will kill bacteria and render enzymes inactive. In addition, the solution should modify tissue constituents in such a way that they retain their form when subjected to treatment that would have damaged them in their initial state. The most commonly used fixative is formalin. In more recent years, alternatives to formalin (formaldehyde) have been proposed. WO 2004/093541 A1 teaches a formaldehyde-free, non-alcoholic tissue preservative composition comprised of ethanedial and a polar aprotic solvent in aqueous solution. Other non-formalin based fixatives include glutaraldehyde, alcoholic solvents, or acetic acid.

Typically after fixation, the sample is often removed from the container, placed in a cassette, and embedded in preparation for sectioning. Such sectioning of the sample often helps a medical professional properly assess the sample under a microscope (e.g. diagnose relationships between cells and other constituents of the sample, or perform other assessments). In order to properly section the sample, several steps are typically performed to embed the sample within a solid substrate. A commonly used solid substrate may include, for example, paraffin wax, which is used to hold the sample in position while also providing a uniform consistency to further facilitate sectioning with the microtome.

Under existing practices, this fixing, transferring, infiltrating, and embedding must all be done manually, and such manual handling of the sample can increase the likelihood of mis-identifying the sample, cross contaminating the samples, or losing part or all of the sample. Further, as multiple samples may be placed in the same jar, and each sample is merely loosely floating in the fixing agent, information about each sample, such as the orientation of the sample with respect to collection and, which sample was collected from which area of the patient (i.e., 2 mm from mass, 4 mm from mass, 6 mm from mass etc.) may be lost and unavailable to the medical professional when assessing the sample. Additionally, the numerous steps of manual manipulation can often increase the time that it takes to provide a proper assessment for each sample, once the sample is collected from the patient.

In the practice of histopathology and the preparation of cellular tissue materials for examination with the microscope, preparatory steps have an important impact on the availability of microscopic details that form the basis of proof for a diagnosis. For example, it may be critical to maintain orientation of the tissue sample during the preparatory phases. In addition, movement of the sample during preparation, either during collection and transfer to the lab or during laboratory processing in a tissue processing cassette, may damage the sample.

When tissue materials are collected, as with a tissue, there are specific criteria or judgments made of what might be suspicious of showing a disease process. The suspect area of the tissue is sampled with the intention of revealing a tissue diagnosis as the basis of a treatment method or approach. Contemporary methods of tissue biopsy and means for providing imaging of hidden suspect tumor targets deep within body cavities or organs, include, in the most modern approach, use of image guidance techniques, direct vision for surface lesions where a biopsy of tissue surfaces are harvested, needle through cut biopsies, aspiration biopsies of fluid, incision biopsies of surface lesions, remote skinny needle biopsies with ultrasound, or MRI, direct video or radio-graphic guidance to an imaging system. The resultant captured tissue may be solid, semi-solid, or liquid, as with cavity fluids containing traces of surface cells, to be determined benign, malignant, or inflammatory. In some instances, core needle biopsies are preferred.

It is of vital importance to orient the tissue in a fixed and precise way that will demonstrate anatomical relationship of importance to adjacent organ tissues or surfaces; all in relationship to the disease process. For instances, if a gastroenterologist or any other special-ologist visualized a suspicious area to biopsy, the ologist alone knows what was up or down, right or left, adjacent the stomach or other anatomical landmark.

WO0019897 teaches that typically prior to the fixation stage, a lab technician will place the tissue samples into the tissue cassette for processing. When the tissue samples are placed in the tissue cassette, the tissue samples are oriented with a specific surface facing up. Generally, the person retrieving the tissue sample after processing and before embedding the tissue sample, will place the surface facing up in the tissue cassette face down in the wax mold for embedding. Thus, maintaining the orientation of the tissue sample after the fixation stage is critical to ensuring that the tissue sample is oriented properly in the wax mold for sectioning.

For example, as taught in WO0019897 maintaining orientation is especially critical for vessel tissue samples where the section needs to be transverse, core biopsy tissue samples where the tissues should lie flat in the same plane, and gall bladder tissue samples where the tissue samples should be embedded on the edge. Critical to maintaining the orientation of a tissue sample may be maintaining proper position of all sides of a tissue sample, for example, face-up/face-down; left/right; or north/south.

Using a single container to maintain orientation of tissue samples from different locations sites may be difficult as tissue samples from different location sites are different shapes and sizes. That is, tissue samples are different shapes and sizes depending on the location from where the tissue sample was removed. For example, fine need aspiration biopsy tends to be very small pieces of tissue taken from the core of a fine needle, whereas, GI biopsy samples are characterized by a few small tissue pieces.

Consequently, it is desired to produce a container to retain, orient, and prevent cross contamination of a different types of tissue samples during the preparatory phases of a histological examination.

Also in consideration is the ischaemic time for pathology samples. That is, it is desirable to quickly preserve the tissue because the faster the tissue is preserved, the better the tissue is for IHC testing. It is further desirable to have a tissue container that allows for time, temperature, and PH monitoring. Also, it is desirable to have a container with an identifier or label that can be tracked and traced during transportation, such as a smart container.

SUMMARY OF THE INVENTION

This invention provides a container which can address some of the problems described above. Example embodiments of this invention may address one or more of the above identified issues. However, an embodiment of this application need not solve, address, or otherwise improve on existing technologies.

One or more embodiments of the invention may include a tissue sample container, including a base having a plurality of sample holding sections, which are configured to receive a plurality of tissue samples in a given orientation, said sample holding sections being shaped and sized to receive a tissue specific tissue sample; a lid configured to sealingly engage the base and in cooperation with the sample holding sections, maintain the given orientation and identity of the tissue samples within the respective sample holding sections.

Use of the container of the invention allows tissue processing, including fixation, after orientating the tissue. After the tissue sample is orientated, the tissue sample is ready for tissue processing, such as such as fixation. The fixing step may comprise applying a solution of fixative such that cross-links are formed in the orientating composition thereby rendering the orientating composition substantially insoluble during subsequent steps of the tissue handling procedure and thereby ensuring the tissue sample remains affixed to the surface of the tissue handling device during the subsequent steps of the tissue handling procedure but remains permeable to all the processing solutions. During fixative, it is desirable that the fixative be contacted with the tissue in a manner that allows for penetration of the fixative into the tissue. Ideally, the tissue remains substantially uncompressed during the fixation to allow adequate penetration of the fixative and to preserve cellular morphology and structure.

DETAILED DESCRIPTION OF THE DRAWINGS

In the following detailed description, reference will be made to the accompanying drawing(s), in which similar elements are designated with similar numerals. The aforementioned accompanying drawings show by way of illustration and not by way of limitation, specific example embodiments and implementations consistent with principles of an example embodiment. These implementations are described in sufficient detail to enable those skilled in the art to practice an example embodiment and it is to be understood that other implementations may be utilized and that structural changes and/or substitutions of various elements may be made without departing from the scope and spirit of an example embodiment. The following detailed description is, therefore, not to be construed in a limited sense.

Figure 1A:
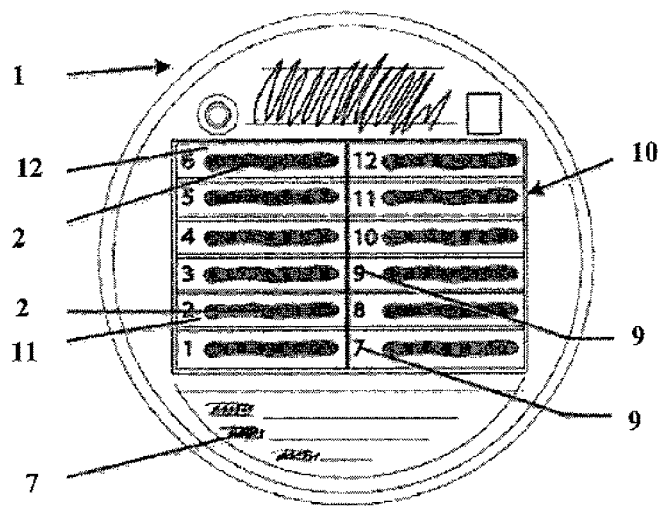
FIG. 1A illustrates a top view of a tissue sample container for according to a first example embodiment of the present application.
Figure 1B:
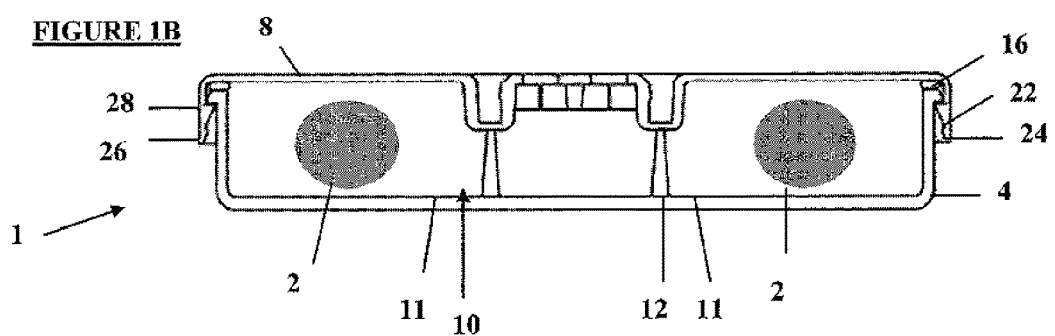
FIG. 1B illustrates a cross-section view of the tissue sample container for according to the first embodiment of the present application.

FIGS. 1A and 1B illustrate a first exemplary embodiment of the instant application. The tissue sample container 1 retains a tissue sample 2 in proper orientation to allow for the automation of the processing and a reduction of human error. As shown in FIG. 1B, a tissue sample container 1, according to one embodiment of the invention, has a base 4, a lid 8, and a sample holding portion 10 which cooperate to retain the tissue sample 2 in a particular orientation, as discussed below.

The base 4 has a bottom surface which may include a sample holding portion 10 and may be divided into a plurality of sample holding sections 11 demarcated by section walls 12 for holding the tissue samples 2 after they are obtained. The sample holding sections 11 may receive an individual sample (i.e. one sample in each section) or a plurality of samples in each section.

The tissue sample container 1 is configured to hold one or more samples 2. In the embodiment shown in FIGS. 1A and 1B, the tissue samples 2 are preferably core biopsy samples. In such instances, the tissue samples 2 may be elongated or otherwise shaped, such that the tissue samples 2 are unable to rotate in the sample holding sections 11 due to the engagement of the lid 8 in cooperation with the section walls 12. Thus, the sample holding sections 11 are configured in shape and size to receive a tissue sample and to maintain its orientation.

Further, when the lid 8 is placed on top of the base 4 the tissue sample container 1 is sealed as discussed in more detail below. Once the tissue sample container 1 is sealed, the section walls 12 in cooperation with the lid 8 sufficiently secures the tissue samples 2 (as shown in FIG. 1B) such that they maintain their orientation within the sample holding sections 11. Once sealed, the tissue sample container 1 can be transported without the tissue samples 2 losing their orientation.

Figure 2A:
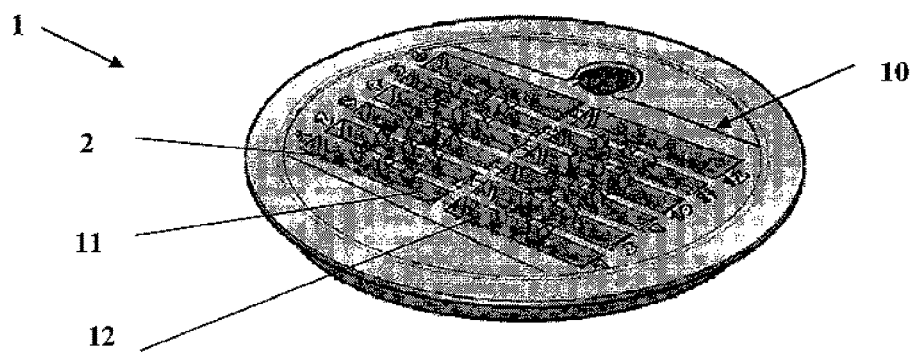
FIGS. 2A-C show a base of the tissue sample container according to certain embodiments in a non-assembled state.
Figure 2B:
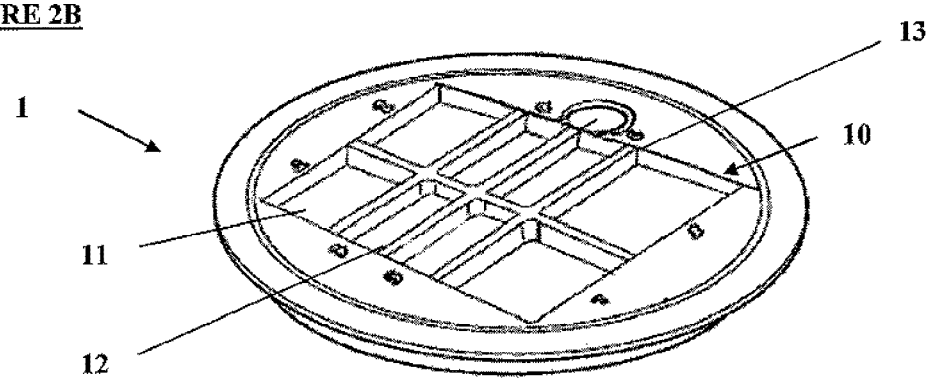
Figure 2C:
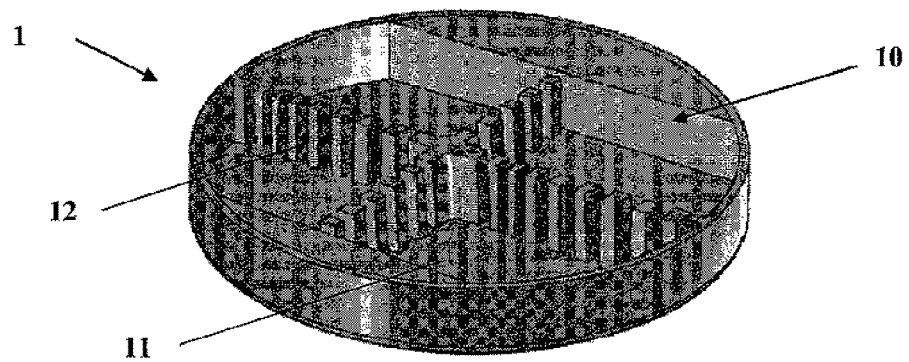

The tissue sample holding sections are not limited to the elongated shape as shown in FIG. 1A. In fact, the size and shape of the tissue holding sections may be tissue specific. For example, the tissue holding sections 11 for core biopsy sample might be long and narrow, while the tissue holding sections 11 for skin tissue might be shorter and wider. FIGS. 2A-2C illustrate some additional shapes and sizes contemplated for the tissue sample holding sections 11 depending on the specific tissue contained in the tissue container 1. The shapes and sizes of the tissue sample sections 11 are not limited to these configurations. Also, the tissue sample container 1 may have one or more sample holding sections 11 each differently sized and shaped to receive a tissue sample 2 and retain the tissue sample 2 in a fixed orientation while the tissue sample 2 is in the container as shown in FIG. 2B.

For transport, the tissue sample container 1 is sufficiently sealed to secure the tissue samples 2 in a non-limiting embodiment. As shown in FIG. 1B the tissue sample container 1 may have a sealing gasket 16 (also illustrated in FIG. 5A). The sealing gasket 16 is not particularly limited and may be a rubber gasket, a plastic gasket, an O-ring, or any other sealing member as would be apparent to a person of ordinary skill in the art. In addition, the connection between the base 4 and the lid 8 is not particularly limited and may include one or more of a tongue and groove configuration, a threaded configuration, a snap fitting configuration, a pressure fitting configuration or any other configuration as would be apparent to a person of ordinary skill in the art.

An example of a sealing mechanism is shown in FIG. 1B. In this embodiment, the connection between the base 4 and the lid 8 may have a two-part closing system with a temporary closed position and a permanently closed position. FIG. 1B shows the permanently closed position. In the temporary closed position, the base 4 has a first lock 22 and second lock 24 and the lid 8 has a first snap 26 and a second snap 28. The first lock 22 and the first snap 26 engage to form the temporary closed position such that the samples may be held in a temporary locked position. In addition, the lid 8 can be further pressed onto the base 4 to a completely locked position such that the first lock 22 engages with the second snap 28 on the base 4 and the second lock 24 engages with the first snap 26 to form the permanently closed position. This permanently closed position forms a fixed closing and further creates a seal at the seal gasket 16. In a non-exemplary embodiment the lid 8 and the base 4 can only be removed by peeling away a part of the lid 8 to release the permanently closed position.

Figure 8:
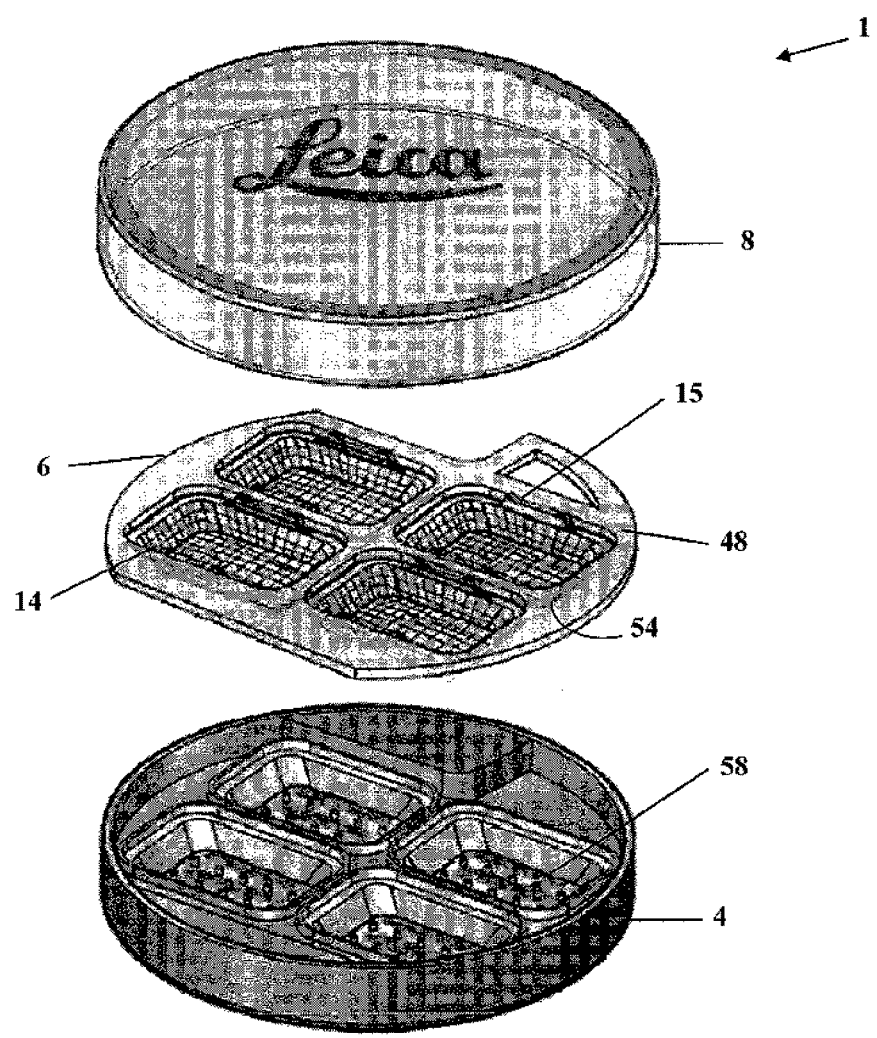
FIG. 8 is an exploded view of the tissue sample container according to one embodiment in a non-assembled state.

Alternatively, the lid 8 may be sealed to the base 8 as the lid 8 is made out of heat sealable film 29 (illustrated in FIG. 8). In this instance the heat sealable film 29 is attached to the base 4 in a heat sealable manner.

Once the tissue sample container 1 is sealed, it is ready for processing. As described above, a tissue sample 2 is processed with a fixing agent to fix and preserve the sample before analysis. The tissue sample container 1 may have fluid dispensing mechanism 30 or a means for processing the tissue samples 2 without disengaging the lid 8 from the base 4. Thus, formalin can be inserted at the top or bottom of the tissue sample container 1 and can penetrate around the tissue samples 2 even with the lid 8 and base 4 closed. This reduces the human exposure to formalin. The following is a description of different fluid dispensing mechanisms 30 with reference to FIGS. 3A, 3B and 4.

Figure 3A:
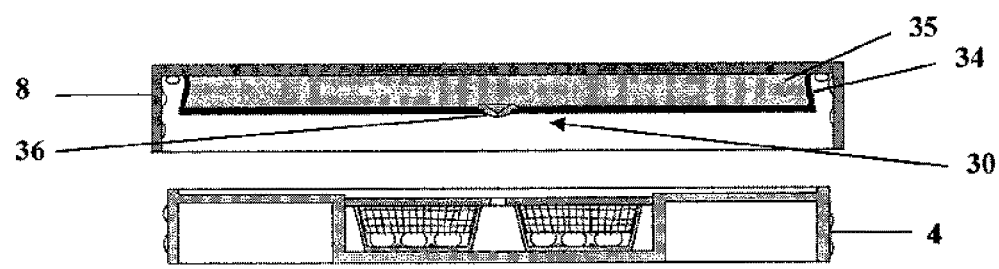
FIG. 3A is a cross-sectional view of one embodiment of the tissue sample container in an unassembled stated.

As shown in FIG. 3A, with the fluid dispensing mechanism may include a pouch 34 containing a fluid 35 that is released into the tissue sample container 1 upon attachment of the lid 8 to the base 4. The fluid 35 in the pouch 34 may be any fluid to preserve and store any tissue samples during transportation, such as formalin. In the embodiment shown in FIGS. 3A-B, the pouch 34 is attached to the inside of the lid 8. The pouch 34 has a frangible portion 36 configured to be broken or ruptured to allow the fluid 35 be released into the tissue sample container 1. The pouch 34 and the frangible portion 36 are designed such that fluid 35 is released when the lid 8 becomes engaged with base 4.

Figure 3B:
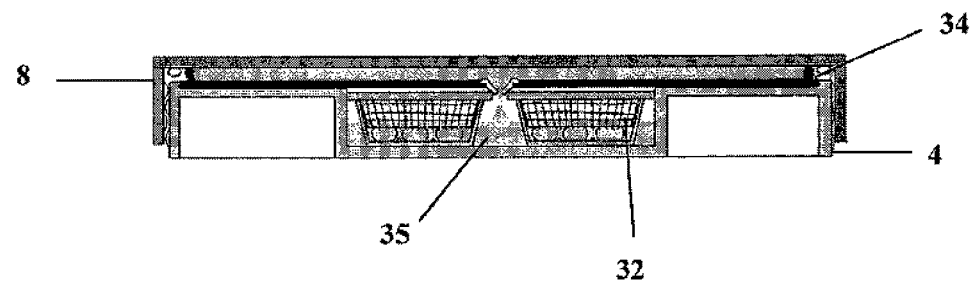
FIG. 3B is a cross-sectional view of the tissue sample container in FIG. 3A in an assembled state.

More specifically, as shown in FIG. 3B, the pouch 34 is disposed directly above the tissue samples 2 and when the lid 8 is lowered onto the base 4, a squeezing force is applied to the pouch 34 as the lid 8 is forced downward. This motion increases the pressure of the fluid within the pouch 34 so that the frangible portion 36 ruptures when the pressure of the fluid 35 exceeds the strength of the frangible portion 36.

Thus, upon engagement of the lid 8 to the base 4, the frangible portion 36 breaks and releases the fluid 35 into the inside of the tissue sample container 1 as shown in FIG. 3B. The fluid 35 is then released into the sample holding sections 11 of the base 4, submerging the tissue samples 2 in the tissue sample container 1.

The frangible portion 36 may be a perforated region or a region formed of a material different from the remainder of the pouch 34, such that the frangible portion 36 of the pouch can be caused to break in a predictable manner. As an example, the lid 8 may be placed upside down to rest on top of the base 4 during transport to prevent inadvertent busting of the pouch 34. The volume of fluid 35 provided is chosen to be sufficient to fill the tissue sample container 1 such that the tissue samples 2 are submerged. Further, in some non-limiting embodiments, a breaking member having, for example, a needle shape and oriented to engage the frangible portion 36 of the pouch 34 and rupture the frangible portion 36 may be provided within the tissue sample container 1.

Figure 4:
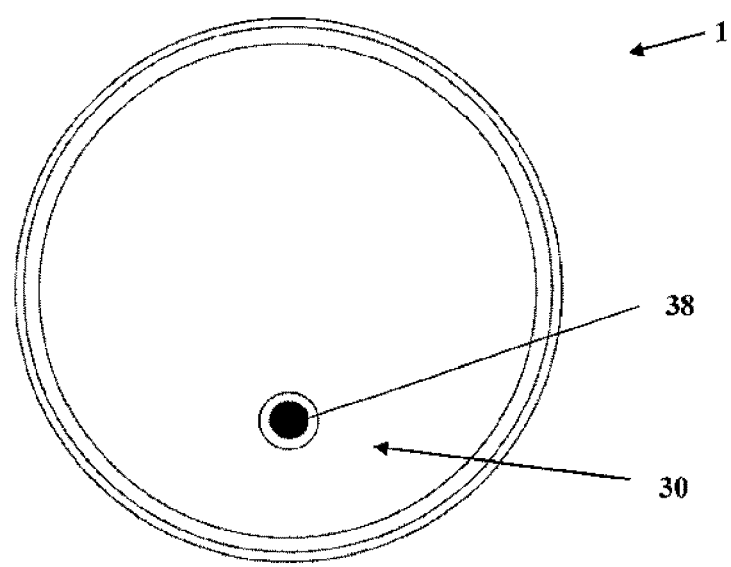
FIG. 4 is a planar view of the tissue sample container according to one embodiment.

Alternatively, as shown in FIG. 4, in one embodiment of the invention, the fluid dispensing mechanism 30 may be a porthole 38 on the lid 8 of the tissue sample container 1. In this instance the porthole 38 may be attached to an external formalin reservoir (not shown in the figures) such that the formalin can be dispensed in the inside of the tissue sample container 1 through the porthole 38. While the porthole 38 is shown in the center of the lid 8, this location is not limiting and the porthole 38 could be located anywhere on the lid 8.

Further, the fluid 35 can pass in between the sample holding sections 10 depending on their size and height. For example in the embodiment shown in FIG. 2B, the section walls 12 are solid and high such that fluid 35 may not be able to pass through the section walls 12. However, in FIGS. 2A and 2C, the section walls are perforated such that fluid 35 may pass through the section walls 12.

Further, in some embodiments, a label 7 or ID tag, may be attached to each tissue sample container 1 as shown in FIG. 1A. Also an identifier 9 may be attached to one or more tissue holding sections 11 configured to receive the tissue sample 2. An important aspect of tissue transportation is properly keeping track of tissue samples. This includes not only tracking the tissue sample containers 1, but also easily identifying the samples 2 within a container.

Figure 7:
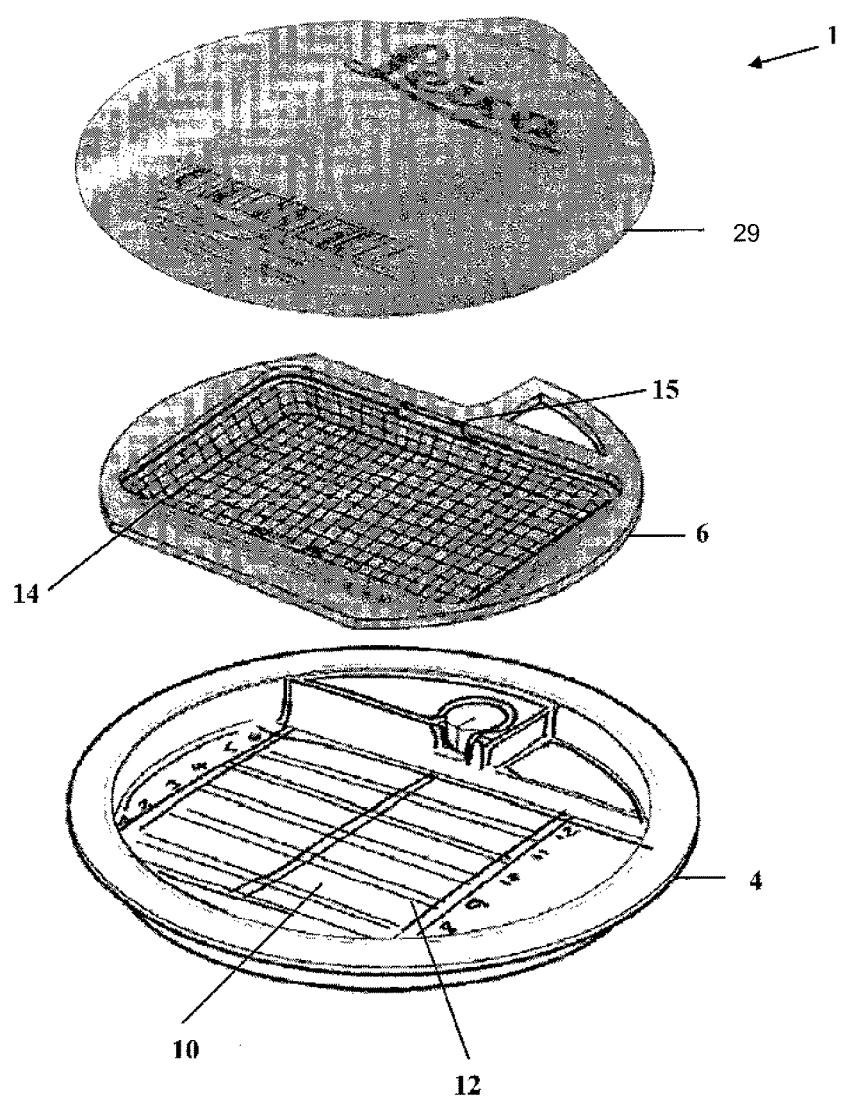
FIG. 7 is an exploded view of the tissue sample container according to one embodiment in a non-assembled state.

In FIG. 1A, the label 7 is shown disposed on the base 4; however, the label 7 can be located anywhere on the tissue sample container 1. (An example of the label 7 on the lid 8 is shown in FIG. 7.)

In the embodiment shown in FIG. 1A, a single label 7 is present; however more than one label 7 may be present and the labels can be physically separated or located together. There also can be a label 7 for each tissue sample container 1 as well as for each tissue sample 2 in the tissue sample container 1. Thus, one or multiple labels 7 can be placed in the sample holding sections 11, the lid 8, the base 4, or another area of the tissue container 2.

In the embodiment shown in FIG. 1A, an identifier 9 is associated with each tissue holding section 11 to more easily identify the samples within the tissue container. Also, the identifiers 9 may help identify the orientation of the tissue sample 2. For example, the identifiers 9 as shown in FIG. 1A may provide guidance as to the north/south or left/right orientation of the tissue sample with respect to the identifier 9.

The label 7 or the identifier 9 may be a computer readable tag including, but not limited to, labels having an incorporated RFID, labels having an incorporated one-dimensional barcode (1-D barcode), labels having an incorporated two-dimensional barcode (2-D barcode), and labels having an incorporated three-dimensional barcode (3-D barcode). However, the computer readable label is not limited to RFID, 1-D barcode, 2-D barcode, or 3-D barcode labels and may include any type of label readable by a computer as would be apparent to a person of ordinary skill in the art.

In some embodiments, a label 7 or identifier 9 is present that may be sensitive to changes to the sample or to the tray itself. For example, the label 7 or identifier 9 may be present that changes physical (i.e. color) or chemical (i.e. redox, conjugation, etc.) properties during fixation of the sample. Similarly, a label 7 may be present that is sensitive to the processing steps which precede embedding (i.e. dehydration). Alternatively, the label 7 or identifier 9 present that is sensitive to the embedding step (i.e. infiltration of wax). The label 7 or identifier 9 may have a property that changes incrementally or switches when the step is complete. In this way, the technician, or an automated system, will be able to determine when the sample has finished one step before another is started.

The tissue sample container 1 of any embodiment of the present application may be formed from a variety of materials and their construction is not particularly limited. Further, an embodiment of this tissue sample container 1 may be constructed from a material having one or more of the following features: transparent on imaging or with minimal interference (i.e. radio transparent), resistant to chemical fixatives (such as formalin), resistant to degradation from chemicals used in tissue processing (such as alcohol, xylene or acids), and resistant to temperatures used in tissue embedding.

In addition, the lid 8 may include a coating on a surface which faces the tissues. The coating is such that is reduces the adhesion between the tissue sample and the tissue facing surface. In non-limiting embodiments, the coating can be a Teflon coating, including Polytetrafluoroethylene (PTFE) coating or the coating can be Polyproplyene (PP).

In a second embodiment of the instant Application, the same base 4 may be used for a variety of differently sized and shaped sample holding sections 11. As such, the section walls 12 may be removable from the base 4 and the tissue sample container 1 may be used to retain the orientation of a variety of different tissue specific tissue samples. In this embodiment an insert 13 (having the same shape as the outline of the section walls 12) is contemplated that may be inserted into the base 4 to form tissue specific tissue sample holding sections 11.

In this embodiment, a kit may be provided which has multiple inserts 13 with a variety of sized and shaped tissue specific sample holding sections 11. Each, tissue specific sample holding section 11 of the insert 13 may be shaped and sized to sufficiently maintain the orientation of the tissue specific tissue sample 2 in the tissue container 1. That is, the inserts 13 in cooperation with the lid 8 maintain the orientation of the tissue specific sample since they are shaped and sized according or the sample size of the tissue sample.

Figure 5A:
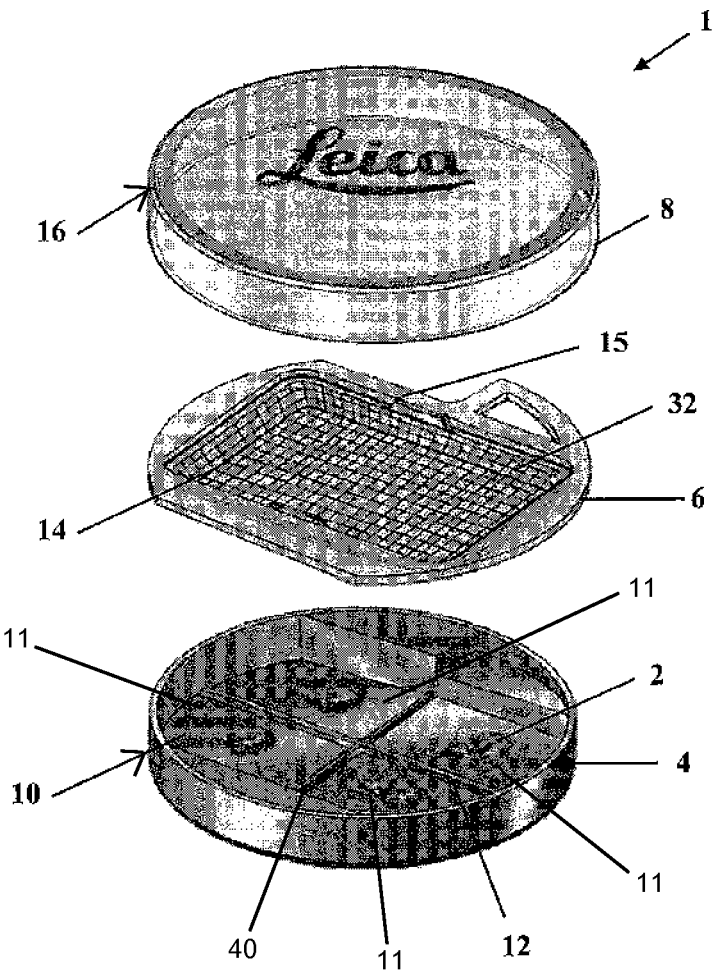
FIG. 5A is an exploded view of a tissue sample container according to a first embodiment in a non-assembled state.
Figure 5B:
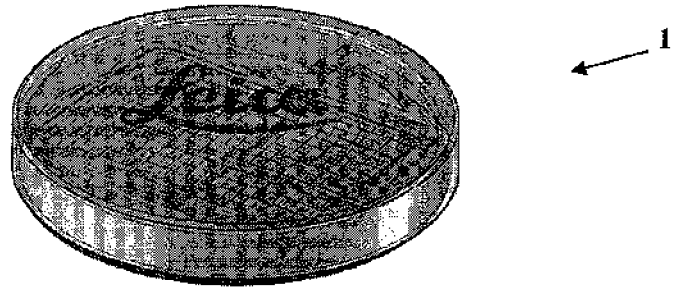
FIG. 5B shows the tissue sample container of FIG. 1A in an assembled state.

FIGS. 5A and 5B illustrate a tissue sample container 1 according to a second embodiment of the present application. The second embodiment mirrors the first embodiment with a few differences. First, a tissue sample container 1 according to a second embodiment of the application, includes a retaining member 6 which cooperates with the base 4 and the lid 8 to retain the tissue sample 2 in a particular orientation, as discussed above. Second, the tissue sample holding sections 11 are demarcated by boundary ribs 40 as opposed to section walls 12 in the above example. The boundary ribs 40, in an exemplary embodiment, are shorter in height than the section walls 12. As such, the boundary ribs 40 in cooperation with the retaining member 6 maintain the orientation of the tissue samples 2. In all other aspects the second embodiment is similar to the first embodiment.

Figure 6:
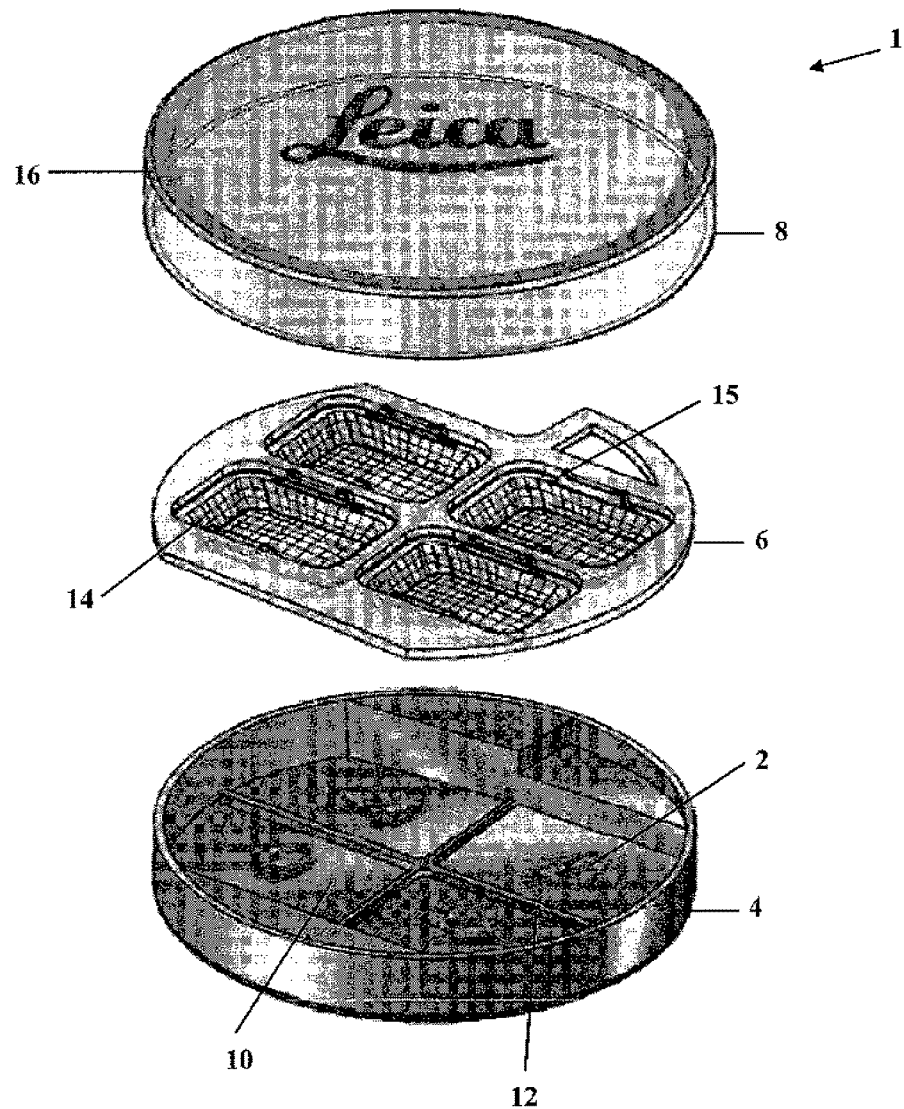
FIG. 6 is an exploded view of a tissue sample container according to another embodiment in a non-assembled state.

The retaining member 6 is configured to be inserted over the base 4 as shown in FIG. 5A such that the retaining member 6 at least partially covers the sample holding sections 11. The retaining member 6 may have a single retaining element 14, as shown in FIG. 5A or a plurality of retaining elements 14, as shown in FIG. 6. In the example shown in FIG. 6, the retaining member 6 includes a plurality of retaining elements 14 corresponding in number and in alignment with the sample holding sections 11.

In an non-exemplary embodiment, each retaining element 14 has a mesh structure and is moveably attached to retaining member 6 by a biasing element 15. In this embodiment, there is a biasing element 15 on opposite sides of each retaining element 14. When the retaining member 6 is secured to the base 4, the biasing element 15 urges the retaining element 14 downwardly towards the sample holding sections 10. In one embodiment, the biasing element 15 urges the retaining elements 14 downwardly against the tissue samples 2 so that the tissue samples 2 are retained between the retaining member 6 and the base 4 to maintain the proper orientation of the tissue samples 2.

Alternatively, the retaining elements 14 may urge against the boundary ribs 40 to provide a slight space between the tissue sample 2 and the retaining element 14 so that the retaining element 14 and the boundary ribs 40 cooperate to hold the tissue samples 2 in place. In such instances, the tissue samples 2 may be elongated or otherwise shaped, such that the tissue samples 2 are unable to rotate in the sample holding sections 10 due to the engagement of the boundary ribs 40 and the retaining element or elements 14.

Similar to the embodiment described above, the lid 8 is placed on top of the base 4 to seal the tissue sample container 1. Once the tissue sample container 1 is sealed, boundary ribs 2 in cooperation with the retaining element 14 sufficiently secures the tissue samples 2 such that they maintain their orientation within the sample holding sections 11, and the tissue sample container 1 can be transported without the tissue samples 2 losing their orientation.

FIG. 5A shows four sample holding sections 11; however, the sample holding sections are not limited to this number. Also, as an alternative to the above, the base 4 may incorporate the biasing element to bias a portion of the base against the tissue samples 2 to sufficiently hold the tissue samples' given orientation depending on the shape and size of the tissue sample 2. Further, the boundary ribs 40 are shown in FIG. 5A to extend in both the longitudinal and latitudinal direction of the base 4 such that the boundary ribs 40 cross to form substantially rectangular sample holding sections 11. The sample holding sections 11 are not limited to this shape and the boundary ribs 40 may extend in only one direction.

Similar to the embodiment above, the fluid 35 may be dispersed inside the container. The retaining member 6 may have a plurality of perforations 32 to allow the fixing agent to flow freely in the container 1. Thus, the fluid 35 released into the tissue sample container 1 can pass through the retaining member 6 to the tissue samples 2 in the sample holding sections 11. In the instances, where a porthole 38 is used for administering the fluid 35 the porthole 38 may also be connected through the retaining member 6, specifically in instances where the lid is a heat sealable film 29 as discussed above (illustrated in FIG. 7).

As an alternative example, the boundary ribs 40 may have perforated walls to further allow fluid to communicate between the sample holding sections 11. That is, in some instances the boundary ribs 40 may have a height great enough such that they partially or wholly contact the retaining member 6 or retaining elements 14 such that fluid 35 may be prevented from passing from one sample holding section 11 to another. Or, the boundary ribs 40 may have a very small height or have perforations to allow fluid flow between the sample holding sections 11.

Further, FIG. 7 illustrates another example of this embodiment where the boundary ribs have a small height such that they do not contact the retaining member 12 and the sample holding sections 10. In this instance, the retaining member 14 maintains the tissue samples fixed orientation and identity within the tissue sample container 1.

FIG. 8 shows an additional embodiment of the tissue sample container 1 of this application. This embodiment is the same as the embodiments described with respect to FIGS. 5A, 5B, 6, and 7 except in this embodiment, the base 4 or the retaining member 6 is configured, to urge towards the tissue samples 2 to clamp or engage the tissue samples. Similar to other embodiments, the retaining member 6 can contact the boundary ribs 40 and not urge directly against the tissue samples.

In the example shown in FIG. 8, the retaining member 6 includes a frame portion 48 and a plurality of retaining elements 14 corresponding in number and in alignment with the sample holding sections 11. In an non-exemplary embodiment, the retaining elements 14 have a mesh structure and are moveably attached to the frame portion 48 by a biasing element 15 respectively provided on opposite sides of each of the retaining elements 14. When the retaining member 6 is secured to the base 4, the biasing element 15 urges the retaining elements 14 downwardly away from the frame portion 48 and toward the sample holding sections 10. The bottom facing surfaces of the retaining elements 14 define a first tissue engaging surface 54 for respectively engaging the tissue sample 2. Further, the top surface of the base 4 defines a second tissue engaging surface 56 for receiving the tissue samples 2. The biasing element 15 urges the retaining elements 14 downwardly towards or against the tissue samples 2 so that the tissue samples 2 are retained between a first tissue engaging surface 54 of the retaining elements 14 and the second tissue engaging surface 56 of the base 4 to maintain the proper orientation of the tissue samples 2.

As shown in FIG. 8, according to this embodiment the retaining member 6 includes a plurality of retaining elements 14. However, the retaining member 6 may comprise only one retaining element 14, similar to the retaining member 6 as described with respect to FIG. 5A.

In addition, as shown in FIG. 8, the base 4 may comprise a plurality of molds 58 which receive the tissue sample 2. In this embodiment the sample 2 is retained between the surface of the mold 58 and the retaining elements 14.

As mentioned above, the retaining element 14 is attached to the frame portion 48 by a biasing element 15. That is, the biasing element 15 is attached at one end to the frame portion 48 and to the retaining element 14 on the other end. The biasing element 15 is configured to provide relative movement of the retaining element 14 with respect to the frame portion 48. The biasing element 15 urges the retaining element 14 towards the base 4 to maintain the tissue samples' orientation. Thus, the biasing element 15 can take on any shape that performs this function. Also in certain embodiments, the retaining elements 14 are movable with respect to the frame portion independently of other retaining elements 14.

Figure 9:
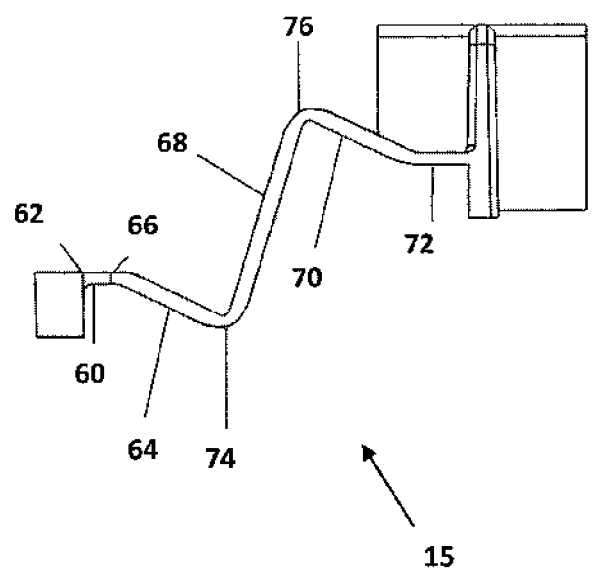
FIG. 9 shows a close-up view of the biasing element in a non-exemplary embodiment of the invention.

One example of the biasing element 15 is shown in FIG. 9 where each biasing element has a substantially S or Z shape. In this example, each biasing element 15 has a first member 60 with a first end 62 and a second end 66. The first end 62 is connected to the tissue retaining element 14. Extending downward at an angle from the second end 66 of the first member 60 is a first angled member 64. A second angled member 68 is connected to the first angled member 64 by a first curved hinged point 74. The second angled member 68 extends upward from the first angled member 64 at an angle; and in a non-limiting embodiment, the second angled member 68 and the first angled member 64 form an angle less than 90°. Extending downward from the second angled member 68 is a third angled member 70. The second angled member 68 and the third angled member 70 are connected by a second curved hinge point 76. In a non-limiting embodiment, the third angled member 70 and the second angled member 68 form an angle less than 90°. Further, in a non-limiting embodiment, the third angled member 70 and the first angled member 64 form an angle less than 90°. A second member 72 connects to the third angled member 70 and extends substantially parallel to the tissue retaining element 14. The second member 72 attaches to the retaining member 6 in a non-limiting embodiment.

Figure 10:
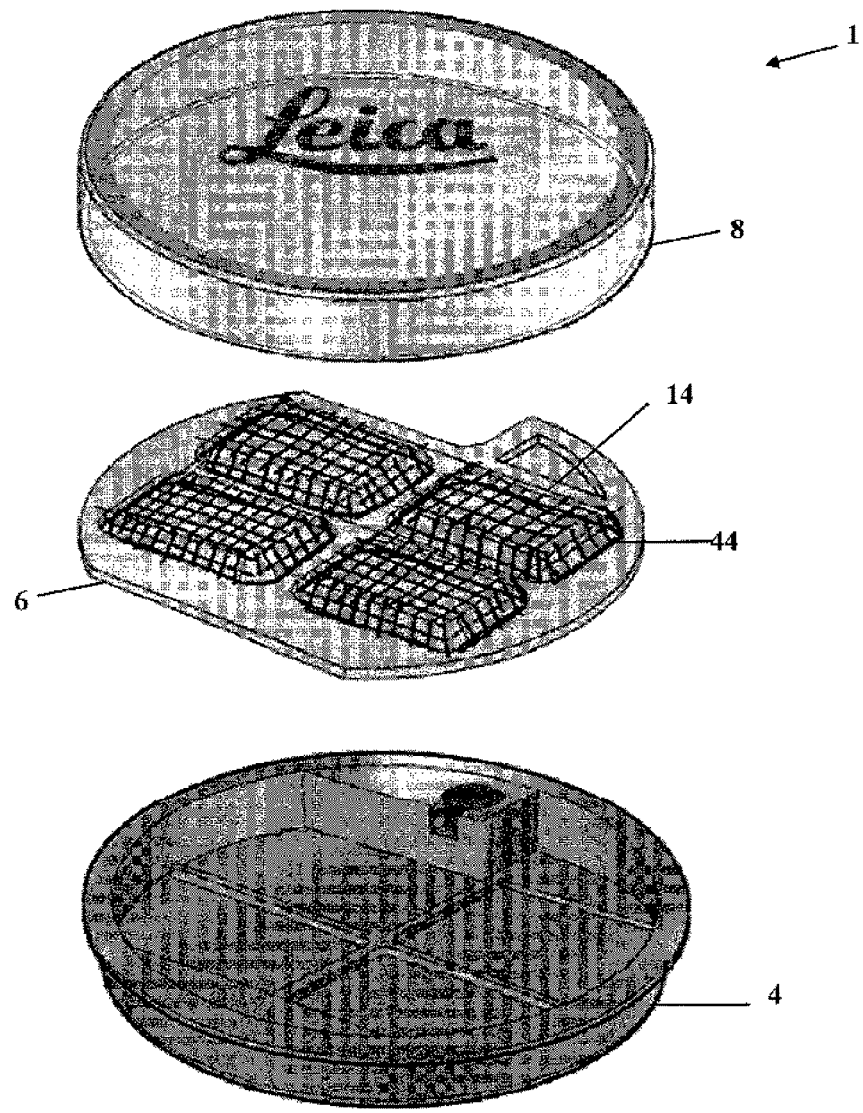
FIG. 10 is an exploded view of the tissue sample container according to one embodiment in a non-assembled state.
Figure 11A:
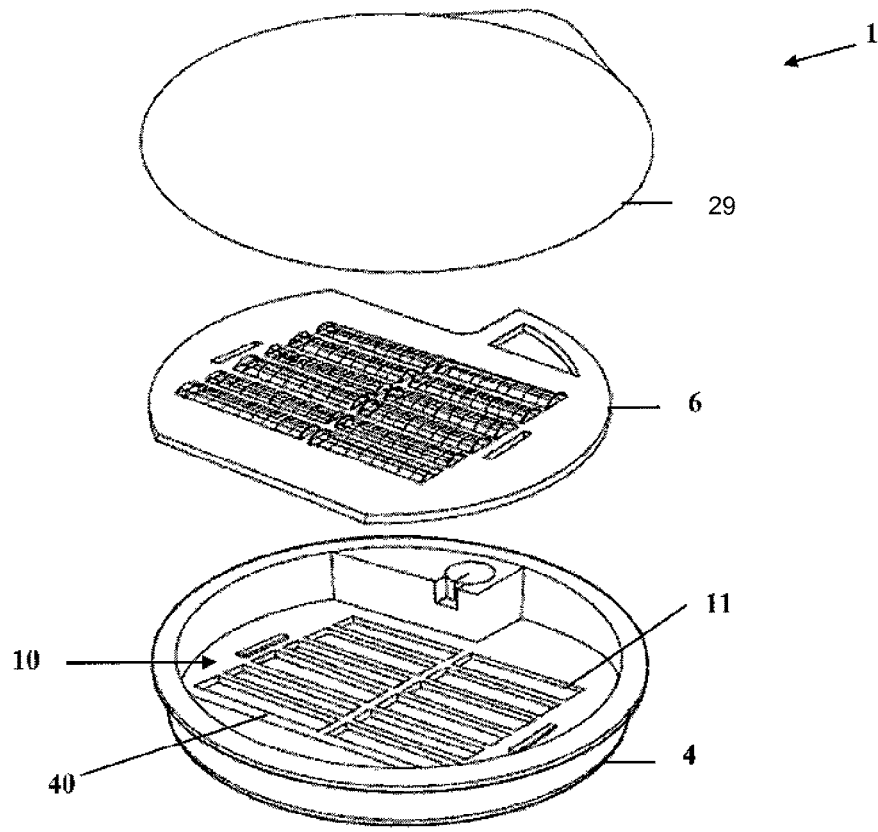
FIG. 11A is an exploded view of the tissue sample container according to one embodiment in a non-assembled state.

FIG. 10 shows an alternate embodiment to the embodiments described with respect to FIGS. 1A, 1B and 2. This embodiment is similar to the embodiments described above, except in this embodiment, the retaining member 6 has retaining elements 14 which extend towards the lid 8 instead of towards the base 4. In this embodiment, the retaining elements 14 have section perimeters 44 which outline each retaining element 14. FIG. 11A illustrates an example where in the section perimeters 44 have a long and narrow shape.

Figure 11B:
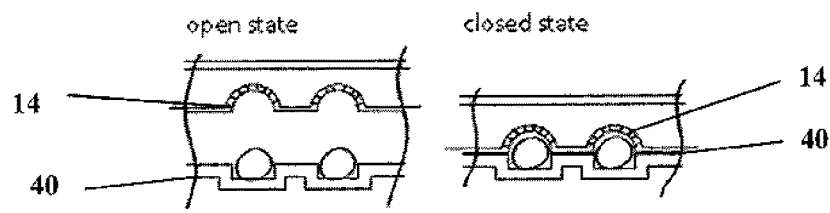
FIG. 11B is a close-up view of the embodiment shown in 11A in an open state and a closed state.

As shown in FIG. 11A, the section perimeters 44 are positioned to partially cover the tissue samples 2 and to align over the boundary ribs 40 on the base 4. The section perimeters 44 can contact the boundary ribs 40 as shown in the close state of FIG. 11B, but they are not limited by this feature. In this example, the tissue sample 2 is sized according to the size of the retaining elements 14, such that the retaining elements 14, in combination with the boundary ribs 40, maintain the tissue sample's orientation.

Although a few example embodiments have been shown and described, these example embodiments are provided to convey the subject matter described herein to people who are familiar with this field. It should be understood that the subject matter described herein may be embodied in various forms without being limited to the described example embodiments. The subject matter described herein can be practiced without those specifically defined or described matters or with other or different elements or matters not described. It will be appreciated by those familiar with this field that changes may be made in these example embodiments without departing from the subject matter described herein as defined in the appended claims and their equivalents. Further, any description of structural arrangement of components or relationship there between is merely for explanation purposes and should be used to limit an example embodiment.

Aspects related to the example embodiment have been set forth in part in the description above, and in part should be apparent from the description, or may be learned by practice of embodiments of the application. Aspects of the example embodiment may be realized and attained using the elements and combinations of various elements and aspects particularly pointed out in the following detailed description and the appended claims. It is to be understood that both the foregoing descriptions are an example and are explanatory only and are not intended to be limiting.

What is claimed is:

1. A tissue sample container, comprising:
   a base having a plurality of sample holding sections which receive a plurality of tissue samples in a given orientation, said sample holding sections being demarcated by section walls;
   a lid configured to sealingly engage the base, and
   a fluid dispensing pouch enclosing a fluid and having a frangible portion which is in fluid communication with the inside of the tissue sample container for dispensing a fluid inside the tissue sample container while the lid and the base are engaged,
   wherein the sample holding sections are sized and shaped to correspond to a specific tissue sample size and shape such that the base in cooperation with the section walls, when the sample contacts the section wall, maintains the given orientation and identity of the tissue samples within respective sample holding sections, and
   wherein said pouch is disposed inside the tissue sample container and the frangible portion is configured to release the fluid into the tissue sample container in response to engaging the lid and the base.

2. The tissue sample container according to claim 1, wherein tissue samples are core biopsy samples at the sample holding sections are shaped and sized to maintain the orientation of core biopsy samples.

3. The tissue sample container according to claim 1, wherein the plurality of sample holding sections are each configured to receive one of the pluralities of tissue samples.

4. The tissue sample container according to claim 1, wherein said sample holding sections are in fluid communication with each other.

5. The tissue sample container according to claim 1, wherein said sample holding sections are not in fluid communication with each other.

6. The tissue sample container according to claim 1, wherein the fluid is a fixing agent chemical selected to fix and preserve the tissue samples for analysis.

7. The tissue sample container according to claim 1, wherein said fluid dispensing mechanism is a porthole on the outside of the lid configured to receive said fluid.

8. The tissue sample container according to claim 1, wherein said pouch is disposed in the lid.

9. The tissue sample container according to claim 1, further comprising a label attached to at least one of the lid or the base.

10. The tissue sample container according to claim 9, wherein the label is a computer readable label.

11. The tissue sample container according to claim 10, wherein the computer readable label comprises at least one of a readable writable RFID, a one-dimensional barcode, a two-dimensional barcode and a three-dimensional barcode.

12. The tissue sample container according to claim 11, wherein the computer readable label contains unique information to at least one of the tissue sample container and one of the plurality of tissue samples.

13. The tissue sample container according to claim 12, wherein the unique information includes one or more of patient identification information, sample collection site location information, collection temperature, collection time, and collection conditions.

14. The tissue sample container according to claim 1, further comprising an identifier to identify the tissue samples within the tissue container.

15. The tissue sample container according to claim 1, further comprising an identifier to identify the proper orientation of the tissue container.

16. The tissue sample container according to claim 1, wherein the lid is a substantially cylindrically shaped lid configured to screwingly seal and engage the base.

17. The tissue sample container according to claim 1, further comprising a seal gasket between the base and the lid.

18. The tissue sample container according to claim 1, wherein the lid further comprises a first snap and a second snap configured to respectively engage with a first lock and a second lock on the base to secure the base and lid member.

19. The tissue sample container according to claim 1, the lid comprises a film member.

20. The tissue sample container according to claim 19, wherein the film member is heat scalable.

21. The tissue sample container according to claim 20, wherein the film is attached to the base in a heat scalable manner.

22. The tissue container according to claim 1, wherein the section walls contain perforations to define the plurality of sample holding sections and allow the sample holding sections to be in fluid communication with each other.

23. The tissue sample container according to claim 1, wherein the section walls prevent the plurality of tissue samples from passing between respective sample holding sections.

24. The tissue sample container according to claim 1, wherein the sample holding sections are differently sized and shaped to correspond to respective differently sized and shaped tissue samples.

* * * * *